United States Patent
Magnusson et al.

(10) Patent No.: US 7,859,257 B2
(45) Date of Patent: Dec. 28, 2010

(54) SYSTEM AND USE CONCERNING UNDER WATER EDDY CURRENT MEASUREMENTS ON COMPONENTS FOR NUCLEAR REACTORS

(75) Inventors: Kurt-Åke Magnusson, Skultuna (SE); Laust Pedersen, Uppsala (SE); Lennart Ahlén, Uppsala (SE); Bjorn Näsström, Vasterás (SE); Holger Wiese, Schönenwerd (CH)

(73) Assignee: Westinghouse Electric Sweden AB (SE)

( * ) Notice: Subject to any disclaimer, the term of this patent is extended or adjusted under 35 U.S.C. 154(b) by 429 days.

(21) Appl. No.: 11/997,785

(22) PCT Filed: Jun. 16, 2006

(86) PCT No.: PCT/SE2006/050202

§ 371 (c)(1),
(2), (4) Date: Apr. 22, 2008

(87) PCT Pub. No.: WO2007/053100

PCT Pub. Date: May 10, 2007

(65) Prior Publication Data

US 2008/0278155 A1    Nov. 13, 2008

(30) Foreign Application Priority Data

Aug. 24, 2005   (SE) .................................. 0501869

(51) Int. Cl.
*G01R 33/12*    (2006.01)
*G01B 7/06*     (2006.01)
*G01N 27/72*    (2006.01)
*G21C 17/00*    (2006.01)

(52) U.S. Cl. ...................... 324/229; 324/239; 324/240; 376/245

(58) Field of Classification Search .............. 324/222, 324/223, 228, 229, 230, 231, 234, 239, 240, 324/262, 238; 376/245, 249, 252, 253
See application file for complete search history.

(56) References Cited

U.S. PATENT DOCUMENTS

| | | |
|---|---|---|
| 4,986,953 A | 1/1991 | Bernard |
| 5,889,401 A | 3/1999 | Jourdain et al. |
| 6,273,019 B1 | 8/2001 | Ciamillo, II |

(Continued)

FOREIGN PATENT DOCUMENTS

DE    2844747 A1    4/1980

(Continued)

*Primary Examiner*—Kenneth J Whittington
(74) *Attorney, Agent, or Firm*—Michaud-Kinney Group LLP

(57) ABSTRACT

The invention concerns a system suited for carrying out eddy current measurements on components for nuclear reactors when these components are located in water. The system comprises a control unit, a measurement probe and a first cable suited to constitute at least a part of the connection between the control unit and the measurement probe. The system also comprises a switching unit, suited to be located in water and arranged to be connected with said first cable, and to be connected with the measurement probe. The switching unit has a switching device which can assume at least a first and a second state. In the first state, the first cable is connected with the measurement probe. In the second state, the first cable is not connected with the measurement probe. The invention also concerns the use of the system.

25 Claims, 2 Drawing Sheets

U.S. PATENT DOCUMENTS

| | | | |
|---|---|---|---|
| 6,369,566 B1 * | 4/2002 | McClelland | 324/229 |
| 6,402,539 B1 | 6/2002 | Toth et al. | |
| 6,429,646 B1 * | 8/2002 | Han | 324/202 |
| 6,541,946 B1 | 4/2003 | Chen et al. | |
| 6,541,964 B1 * | 4/2003 | Jourdain et al. | 324/232 |
| 6,640,635 B2 * | 11/2003 | Nakatsuka | 73/643 |
| 6,640,901 B1 | 11/2003 | Appleford et al. | |
| 6,850,077 B2 * | 2/2005 | Slates | 324/693 |
| 7,019,579 B2 * | 3/2006 | Bolz et al. | 327/374 |
| 2002/0071513 A1 | 6/2002 | Uckert | |
| 2002/0075984 A1 | 6/2002 | Knecht et al. | |
| 2004/0083940 A1 | 5/2004 | Shelton et al. | |
| 2007/0279050 A1 * | 12/2007 | Edsinger et al. | 324/222 |

FOREIGN PATENT DOCUMENTS

EP      0545551 A2    6/1993

* cited by examiner

SYSTEM AND USE CONCERNING UNDER WATER EDDY CURRENT MEASUREMENTS ON COMPONENTS FOR NUCLEAR REACTORS

FIELD OF THE INVENTION

The invention concerns a system suited for carrying out eddy current measurements on components for nuclear reactors when these components are located in water. The system is adapted to measure at least one property of these components, such as the thickness of at least one layer located on the component, by generating at least one electromagnetic alternating field which penetrates the component in question and in the same generates eddy currents which retroact on the generated electromagnetic alternating field. The system is arranged to carry out the measurement of the property in question by measuring a response to the generated electromagnetic alternating field and carrying out a calculation of the property in question. The system comprises at least:

a control unit, intended to be located outside of the water and arranged to control the measurement, a measurement probe suited to being moved to the immediate vicinity of the component in the water, wherein the measurement probe comprises means, preferably at least one coil, with the help of which the electromagnetic alternating field which penetrates the component in question is generated, and a first cable suited to constitute at least a part of the connection between the control unit and the measurement probe, wherein this cable is suited to at least partially being located in the water.

BACKGROUND OF THE INVENTION

U.S. Pat. No. 5,889,401 and U.S. Pat. No. 6,541,964 describe methods and apparatuses for eddy current measurements on components, for example fuel rods, in nuclear power reactors. As is mentioned in these documents, it can be important to be able to carry out measurements of for example the thickness of layers that may exist on such components. The layer can for example be an oxide layer. Fuel rods for nuclear reactors can also have a layer of another kind, for example a so-called crud layer. The crud layer is usually located outside of the oxide layer. The crud layer can be magnetic, which makes the measurement of the thickness of the oxide layer more difficult. It is, however, possible to measure the thickness of the oxide layer and/or the thickness of the crud layer, even if the crud layer is magnetic, with a suitable calculation model, for example of the kind that is described in the above cited documents. The measurement can also be carried out concerning other properties than layer thickness, for example concerning the content of hydrides in the component. The measurement is carried out with a measurement probe which is arranged in the immediate vicinity of the measurement object. The measurement probe is connected with a measurement equipment via at least one cable. The properties of the cable can influence the measurement result, since the cable has a certain transfer function. In connection with measurements, a calibration therefore needs to be carried out, inter alia concerning the influence of the cable on the measurement result, in order to obtain a correct measurement result.

SUMMARY OF THE INVENTION

An object of the present invention is to provide a system of the initially mentioned kind which enables a calibration of the measurement equipment. A purpose is thereby to enable a calibration which takes the influence of the cable on the measurement result into account. A further object is that it shall be possible to carry out this calibration in a relatively simple manner. A still further object is that it shall be possible to carry out the calibration when the measurement probe and the mentioned cable are located under water where the actual measurement is to take place.

These objects are achieved with a system of the initially mentioned kind, wherein the system is characterised in that it also comprises a switching unit, suited to be located in water and arranged to be connected with said first cable, and to be connected with the measurement probe, wherein the switching unit comprises a switching device which can assume at least a first and a second state, wherein in the first state the first cable is connected with the measurement probe and in the second state the first cable is not connected with the measurement probe.

Since the system has such a switching unit, a calibration of the measurement equipment when the measurement probe and said first cable are arranged in water where the measurement is to take place is made possible. The switching unit is thus adapted to be located in water. The switching unit can thus be used for connecting and disconnecting the mentioned first cable from the measurement probe. Since the first cable can be disconnected from the measurement probe, a calibration can be carried out. As has been mentioned above, the first cable can influence the measurement result since the cable has a certain transfer function. The transfer function of the cable is not necessarily constant but can for example depend on how the cable is arranged. The transfer function can thus vary between different measurement occasions. A calibration can thus comprise the determination of the transfer function of the cable. The influence of the cable on the measurement can thereby be removed. During a measurement, normally the impedance of the measurement probe is measured. Since the influence of the cable can be removed, the impedance of the actual measurement probe can be obtained. In other words: it is possible to isolate the impedance of the measurement probe. Such a calibration is made possible since the system comprises the above mentioned switching unit. How the calibration itself is carried out will be described more closely below.

Said control unit preferably comprises means for enabling remote control of the switching device. An operator can thus be located at a distance from the switching unit and remotely control the switching device which forms part of the switching unit.

It should be noted that when a cable is mentioned in the text, this cable can preferably comprise several electric conductors. When it in the description and the claims is mentioned that a certain cable is connected in a certain manner, this suitably thus means that preferably two electric conductors in the cable are connected in the manner that is specified.

Said first cable is preferably relatively long in order to enable measurement at a relatively large distance from the control unit. The first cable is suitably longer than 8 m, for example between 10 m and 30 m.

It should also be noted that when it is stated that the electromagnetic alternating field penetrates the component in question, this does not necessarily mean that the electromagnetic alternating field penetrates the whole component but only that the electromagnetic alternating field penetrates a part into the component in question.

It should also be noted that the coil that suitably exists in the measurement probe for generating the electromagnetic alternating field can also be used for detecting eddy currents which are produced in the component or the retroaction of the eddy currents on the generated electromagnetic alternating field.

According to an embodiment of the system, the switching unit comprises at least a first known load and is arranged such that in said second state the first cable is connected with the first known load. Since the switching unit has such a first known load a calibration measurement can be carried out on the known load. Since during this calibration measurement, the first cable is connected to the known load, the influence of the cable is taken into account during the calibration measurement.

The first known load preferably has a known finite impedance value. The known finite impedance value can for example be between 5 Ω and 1000 Ω, for example 50 Ω. It should be noted that said first known load preferably is such that it has a constant impedance over the whole frequency range where measurements are to be carried out.

According to a further embodiment of the system, the switching unit comprises a second known load, wherein the switching device can assume a third state, wherein in the third state the first cable is connected with the second known load. Since the switching unit has a second known load, the calibration can be improved since said first cable can be connected with the second known load.

The second known load can have essentially the impedance value 0 Ω. The second known "load" can thus constitute a short circuiting.

According to a further embodiment of the system, the switching unit comprises a third known load, wherein the switching device can assume a fourth state, wherein in the fourth state the first cable is connected with the third known load. By using a further known load, the calibration possibilities are further improved.

The third known load can have essentially infinite impedance value. The third known load can thus constitute an open contact. By using three such loads, i.e. short circuiting, open contact and a known finite impedance value, an accurate calibration can be carried out. Preferably also said second "load" and third load are such that they have a constant impedance over the whole frequency range where measurements are to be carried out.

According to a further embodiment of the system, the system comprises a second cable, of a certain length l, wherein one end of the second cable is connected to the switching unit and the other end of the second cable is connected to the measurement probe, wherein in the first state the first cable is connected with the measurement probe via the second cable. The second cable which extends from the switching unit to the measurement probe is preferably relatively short. The length l can for example be between 0.3 m and 3 m, for example between 0.4 m and 2 m, for example about 0.8.

According to a further embodiment of the system, the switching unit comprises a third cable, with the same, or at least essentially the same, characteristics as the second cable, wherein the switching device is arranged such that the first cable can be connected to the third cable instead of to the second cable. Since the third cable has similar characteristics to that of said second cable, the third cable can be used during the calibration.

According to a further embodiment of the system, the third cable has exactly, or at least approximately, the length l. Since the third cable has exactly (or approximately) the same length as the second cable, the influence of the third cable on the measurement during a calibration corresponds to the influence of the second cable during a real measurement on a component. By using the third cable, the calibration can thus "be moved forward" all the way to the measurement probe itself. During the measurement it is thereby possible to isolate the impedance of the measurement probe itself from the influence that the cables leading to the measurement probe have on the measurement.

According to a further embodiment of the system, the switching unit is arranged such that in one, two or all of said second, third and fourth states, the first cable is connected with the known load via the third cable. Since the load in question is connected to the first cable via the third cable, it is obtained, during a calibration measurement with the known load, a result where account has been taken to the characteristics of the second cable (which then is used during a real measurement on a component). In the mentioned second, third and fourth states, the measurement probe is thus preferably not connected with the first cable.

According to a further embodiment of the system, the switching unit has a casing which is constructed not to let in water, such that the parts which are arranged within the casing remain dry when the switching unit is used in water. Within the casing suitably at least the switching device, the loads and the mentioned third cable are arranged. These parts are thus protected by the casing.

According to a further embodiment of the system, the system is arranged with means for introducing a gas, preferably air, within the casing when the system is used and the switching unit is located in water, for causing an overpressure within the casing such that water is prevented from penetrating into the inside of the casing. By introducing air within the casing it is further ensured that the parts that are within the casing are maintained dry.

According to a further embodiment of the system, the system comprises a measurement probe holder which is arranged to be able to move the measurement probe to and from the component on which it is to be measured. A measurement probe holder or, in other words, a measurement carriage, is thus suitably used for moving the measurement probe.

According to a further embodiment of the system, the system comprises one or more calibration objects, with known properties, located in the vicinity of the measurement probe holder, wherein the measurement probe holder is arranged to be able to move the measurement probe to said one or more calibration objects for enabling a calibration measurement. For further calibration it is an advantage if, in the vicinity of the measurement probe holder, in the water where the measurement on the component is to be carried out, there are calibration objects with known properties. If measurement is to be carried out on a fuel rod, the calibration objects may constitute short fuel rods (or cladding tubes for fuel rods) with known layers of known thicknesses arranged thereon. If measurement is to be carried out for example concerning hydride content in the fuel rods, then the calibration objects can in a similar manner have a known hydride content.

According to a further embodiment of the system, the system comprises remote control means arranged to enable remote control of the movement of the measurement probe holder. An operator who is located at a distance from the measurement probe can thus remotely control the moment of the measurement probe holder and thereby the movement of the measurement probe.

According to a further embodiment of the system, the system comprises a temperature sensor which is adapted to be located next to or in the vicinity of the switching unit or the measurement probe and which communicates with the control unit. The temperature sensor can thus constitute a temperature reference for improving the accuracy of the measurement.

According to a further embodiment of the system, the system comprises a resistance meter, intended to be located outside of the water, and adapted to carry out measurement of direct currant resistance, wherein said resistance meter is adapted to be connected with one end of said first cable at the same time as the second end of the first cable is connected to the switching unit. Such a resistance meter can for example be used for indirectly measure the temperature at the measurement probe (how this is done will be explained below). Such a resistance meter can therefore be used as an alternative, or a complement, to the above mentioned temperature sensor.

According to a further embodiment of the system, the switching unit and the parts which form part thereof are adapted to function in a radioactive environment of the kind which may be the case during measurement in water on components for nuclear reactors. For example, the switching device can be made of relays which are not sensitive to radioactive radiation of such an intensity which may be the case in the environment where the measurement is to be carried out. It can be noted that the switching unit (thanks to the above mentioned second cable) can be located at a certain distance from the component (for example the fuel rod) the property of which is to be measured. Furthermore, the casing can be made of a material which protects against radioactive radiation. The casing can for example be made of aluminium which provides a certain such protection. The relays are preferably of such a high quality that they do not give any significant contribution to the impedance.

According to a further embodiment of the system, the system comprises a further measurement probe adapted to be connected with the switching unit at the same time as the previously mentioned measurement probe is connected to the switching unit. By having a further measurement probe it is for example possible to arrange this further measurement probe at a calibration object at the same time as the previously mentioned measurement probe is arranged at the component itself, the property of which is to be measured. It is hereby possible to carry out a comparative measurement in order to determine the property of the component in question.

The invention also concerns the use of a system according to any one of the above mentioned embodiments. The system is thereby used in such a manner that said components, on which measurement is carried out, are fuel rods for a nuclear reactor. With advantage, the system according to the invention is thus used for a measurement on components in the form of fuel rods. It should be noted that a fuel rod consists of a cladding tube which contains nuclear fuel. When in this document it is said that a measurement is carried out on a fuel rod, it is thus preferably meant that the measurement is carried out on the cladding tube which surrounds the nuclear fuel.

According to one use of the system, measurement of the thickness of at least one layer on a fuel rod is carried out. A suitable use of the system is thus for measuring layer thickness, for example the thickness of an oxide layer on a fuel rod (on the cladding tube which surrounds the nuclear fuel).

According to a further use of the system, a measurement is carried out of the hydride content in the fuel rod. As previously mentioned, the system can also be used for measuring the hydride content in a fuel rod (in the cladding tube which surrounds the nuclear fuel).

According to a further use of the system, the measurement is carried out when the fuel rods are located in a water pool. A nuclear fuel plant usually has a water pool where fuel assemblies with fuel rods can be stored. The system is suitably used for measurement in such a water pool. The measurement can suitably be carried out at a water depth of more than 5 m.

BRIEF DESCRIPTION OF THE DRAWINGS

FIG. 2 shows schematically that which can form part of the switching unit which forms part of the system according to the invention.

DESCRIPTION OF AN EMBODIMENT OF THE INVENTION

Figure 1:
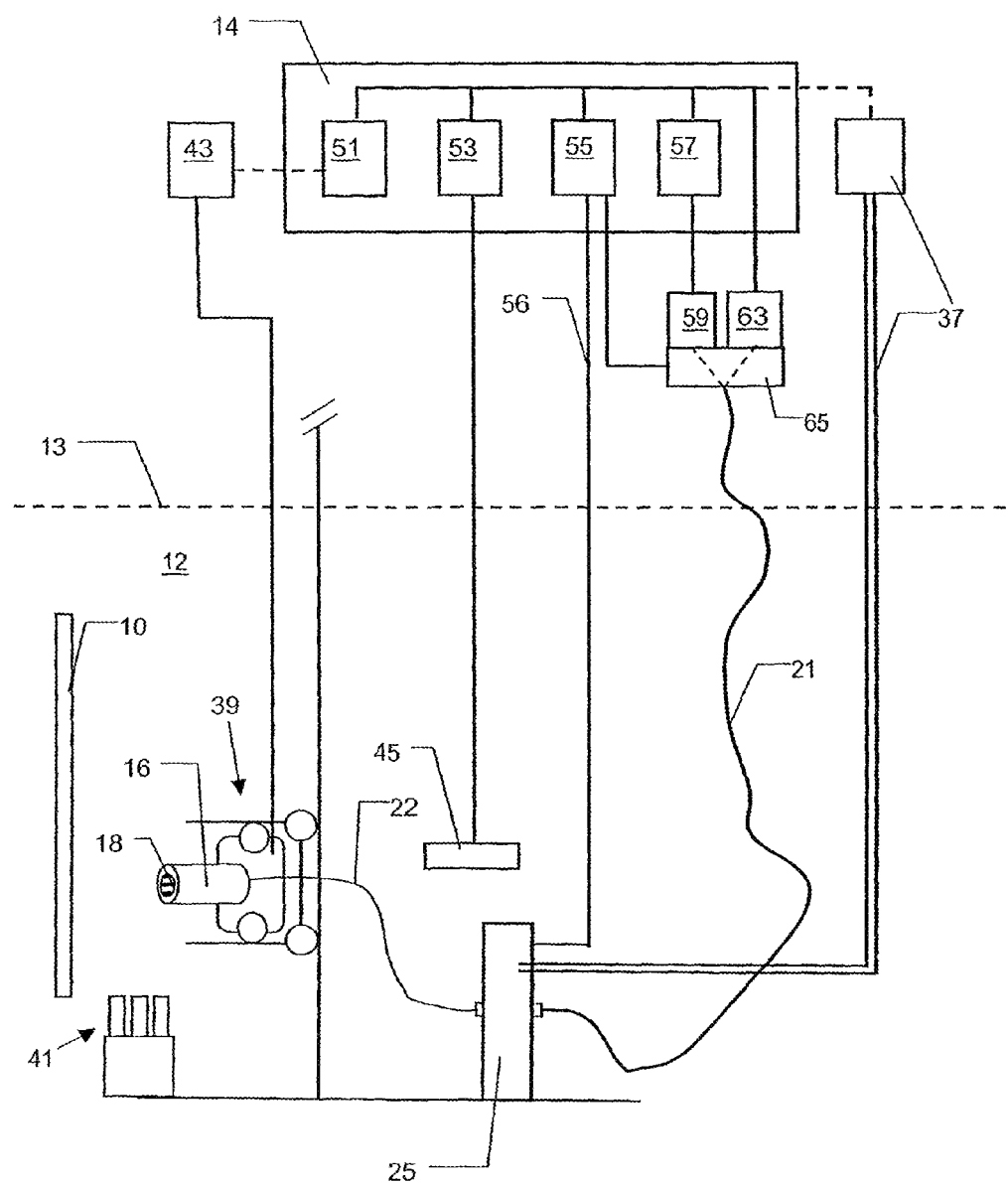
FIG. 1 shows schematically an embodiment of a system according to the invention.
Figure 2:
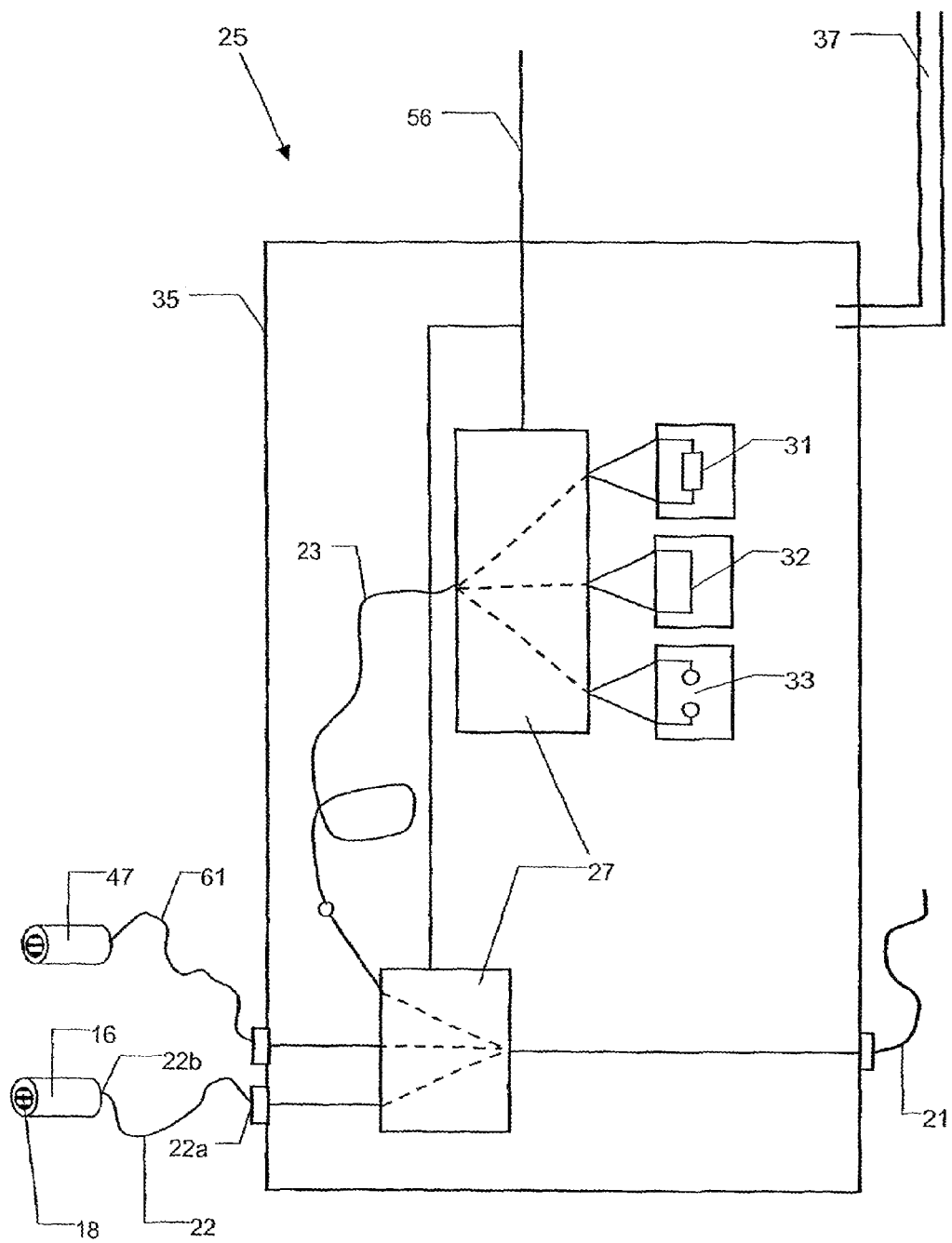
FIG. 2 shows schematically a somewhat more detailed view of a part of the system according to FIG. 1. In particular.

An embodiment of a system according to the invention is thus schematically clear from FIGS. 1 and 2. The figures show a system which is suited for carrying out eddy current measurements on components 10 for nuclear reactors, when these components 10 are located in water 12. The components 10 can for example be fuel rods for a nuclear power reactor. The water 12 can constitute a water pool in which such fuel rods 10 are stored. The water surface 13 is shown with a broken line in FIG. 1. The water pool can have a considerable depth. Suitably, the measurements are carried out at a depth of more than 5 m.

The whole system is suitably arranged for carrying out measurements with the help of an inductive eddy current measurement method on such components 10. For example, the thickness of an oxide layer and/or a crud layer which can exist on such components 10 can be measured with the help of the system according to the invention. It is also possible to use the system for other measurements, for example for measuring the hydride content in the fuel rods 10. The measurement is carried out by moving a measurement probe 16 to the immediate vicinity of the component 10. The measurement probe 16 comprises suitably at least one coil 18, with the help of which an electromagnetic alternating field is generated. The electromagnetic alternating field penetrates into the component 10. Thereby eddy currents are produced in the component 10 which retroact on the generated electromagnetic alternating field. The system is arranged to with the help of the measurement probe 16 measure a response, caused by the eddy currents, on the generated electromagnetic alternating field. The system is thereby arranged to carry out a calculation of the property in question which is to be measured on the component 10. The measurement procedure itself can for example be carried out in the manner that is described in the above cited US patents. Preferably, electromagnetic alternating fields of different frequencies are produced during the measurement. The calculation model can include an iterative process similar to the one described in the above cited documents. However, the present invention is not limited to the calculation process that is described in these documents.

The measurement probe 16 is connected to a control unit 14 with the help of inter alia a first cable 21. The first cable 21 may for example be 15 m long.

The coil 18 which is arranged in the measurement probe 16 can for example be of the kind which is described in the above cited document U.S. Pat. No. 6,541,964.

The system comprises a control unit 14 which is located at a distance from the measurement probe 16 in a space outside of the water 12. The measurement is controlled via the control unit 14. The control unit 14 can comprise a computer 51, a temperature measurement unit 53, a relay drive unit 55 and an impedance analyser 57. The units 53, 55 and 57 are suitably connected with the computer 51.

The impedance analyser 57 can for example be of the kind HP 4294 A. The impedance analyser 57 can be connected to the first cable 21 via an impedance probe 59. The impedance probe 59 may for example be of the kind HP 42941 A.

The first cable 21 is suitably a coaxial cable. The first cable 21 is connected to a switching unit 25. The switching unit 25 is also connected to a first end 22*a* of a second cable 22. The second end 22*b* of the second cable 22 is connected to the measurement probe 16. The measurement probe 16 is arranged in a measurement probe holder 39. The measurement probe holder 39 can be remotely controlled from remote control means 43 which can be arranged in connection with the control unit 14. Possibly, the remote control means 43 can be connected to the computer 51. With the help of the measurement probe holder 39, the measurement probe 16 can thus be moved to and from the component 10 on which it is to be measured. The movement can suitably be supervised with the help of a camera (not shown in the figures).

The system also comprises one or more calibration objects 41. These calibration objects 41 can constitute short parts of cladding tubes for fuel rods. The calibration objects 41 have known properties (for example known layer thicknesses arranged on the calibration objects and/or a known hydride content). The calibration objects 41 are arranged near the measurement probe holder 39. The measurement probe holder 39 can thus be remotely controlled from the remote control means 43 in order to move the measurement probe 16 to one or more of the calibration objects 41. The measurement probe 16 can then of course be moved back to the component 10.

The second cable 22 is for example 0.8 m long. The second cable 22 is suitably constructed such that it can be used in the radioactive environment that is the case near the fuel rod 10.

The system comprises a temperature sensor 45 which is located in the vicinity of the location where the actual measurement is carried out. The temperature sensor 45 is connected with the temperature measurement unit 53. The temperature sensor 45 thus communicates with the control unit 14.

The switching unit 25 can have a casing 35 which is constructed not to let in water inside the casing 35. The casing 35 can for example be made of aluminium or another suitable material which also protects the parts inside of the casing against radioactive radiation. The system can also be equipped with means 37 (for example including an air pump) for conducting air into inside the casing 35 for causing an overpressure within the casing 35. This leads to the fact that water is prevented from penetrating into the inside of the casing 35. The parts which are within the casing 35 are therefore maintained dry.

Within the casing 35 there is a switching device 27. The switching device 27 can consist of relays. The switching device 27 can assume different switching states. Different switching possibilities are schematically indicated with broken lines in FIG. 2. The switching device 27 can be remotely controlled from the relay drive unit 55. The switching device 27 is for example connected with the relay drive unit 55 via a cable 56. The cable 56 is thus a cable for control current to the switching device 27.

In a first switching state, the switching device 27 is arranged such that the first cable 21 is connected, via the switching unit 25, with the second cable 22 and thereby with the measurement probe 16. In a second switching state, the first cable 21 is not connected with the second cable 22 but instead with a third cable 23 and via this third cable 23 with a first known load 31. This known load 31 can have an impedance value of 50 Ω. It should be noted that the cables 21, 22 and 23 suitably comprise at least two electric conductors. In the second state, these two conductors are thus connected to each other via the first load 31.

In a third state, the switching device 27 is arranged such that the first cable 21 is connected to a second known load 32 via the third cable 23. The second known "load" 32 can for example constitute a short circuiting and thus have the impedance value 0 Ω.

In a fourth state, the switching device 27 is arranged such that the first cable 21 is connected to a third known load 33 via the third cable 23. The third known load 33 can suitably have an infinite impedance value, that is, the two conductors in the cables are not connected to each other (open condition).

The third cable 23 suitably has a characteristic and a length l which are the same as for the second cable 22. During a calibration measurement with the known loads 31, 32 and 33 account is thereby taken to the characteristics of the second cable 22 which then is to be used during the real measurement.

With the help of the switching unit 25 a calibration can thus be carried out with the help of the known loads 31, 32, 33. This calibration can be carried out with the switching unit 25 arranged in the same position that it then will have during the actual measurement on the component 10. This means that also the long first cable 21 is arranged in the same manner during the calibration measurement as it will be arranged during the later measurement on the component 10. During the calibration measurement account is thus taken to the influence of the first cable 21 on the measurement. Furthermore, due to the fact that the third cable 23 has the same characteristics as the second cable 22, account is also taken to the characteristics of the second cable 22. With the present invention a very accurate calibration can therefore be carried out. The calibration is suitably carried out at a plurality of frequencies, in a corresponding manner as the measurement on the component 10 then is done at a plurality of frequencies. Through the calibration it is thus possible to eliminate the influence of the first and (with the help of the third cable) the second cable on the measurement result. In other words: it is possible to isolate the impedance of the measurement probe.

In addition to the calibration that is carried out with the help of the known loads 31, 32 and 33, a calibration measurement can also be carried out against the calibration objects 41. Due to the remote control means 43 and the relay drive unit 55 this whole calibration procedure can be remotely controlled. It can be noted that further calibrations can be carried out, for example concerning the impedance probe 59 and the characteristics of the coil 18 itself. These calibrations are however not described in this document.

As a complement or alternative to the above described temperature sensor 45, the system can comprise a resistance meter 63, which is located outside of the water 12. The resistance meter 63 is adapted to carry out measurement of direct current resistance. The resistance meter 63 is adapted to be connected with one end of said first cable 21 at the same time as the second end of the first cable 21 is connected to the switching unit 25. The system can for example be arranged such that said one end of the first cable 21 alternatively can be connected to the resistance meter 63 or to the impedance probe 59. This switching can take place with the help of a relay unit 65. The switching with the relay unit 65 can for example be controlled with the help of the relay drive unit 55. The resistance meter 63 can also be connected with the control unit 14.

The resistance meter 63 can be used for indirectly measuring the temperature at the measurement probe 16 which comprises the coil 18. The resistance of the measurement probe 16 (in particular of the coil 18) is temperature dependent and it is thereby possible to measure the temperature by measuring the resistance of the measurement probe 16. Direct current measurement, with the help of the resistance meter 63, of the resistance of the measurement probe 16 eliminates the influence from its inductance and capacitance.

The resistance of the measurement probe 16 can be isolated by subtracting the resistance of the first cable 21 and the second cable 22 from the total resistance which is obtained when the resistance is measured with the measurement probe 16 connected to the resistance meter 63 via the first 21 and the second 22 cable.

The combined resistance from the first cable 21 and the second cable 22 (without connected measurement probe 16) can be measured with the help of the resistance meter 63 in that the switching device 27 assumes said third state. In this state, the first cable 21 is via the third cable 23 (which corresponds to the second cable 22) connected with the second known "load" 32 (i.e. the short circuiting).

With the help of the resistance meter a method can thus be obtained for indirect measurement of the temperature that is the case at the measurement probe 16. To know the temperature can be important in order to obtain an accurate measurement result during the eddy current measurement.

FIG. 2 also shows that the system can comprise a further measurement probe 47 which is connected to the switching unit 25 via a cable 61 which has the same characteristics and length as the second cable 22. The further measurement probe 47 can be connected with the switching unit 25 at the same time as the previously mentioned measurement probe 16 is connected to the switching unit 25. With the switching device 27 it is possible to control the switching between the measurement probes 16 and 47. The measurement probe 47 can for example be arranged at a calibration object 41 at the same time as the measurement probe 16 is arranged at the component 10 itself. It is also conceivable that the system comprises a measurement bridge (not shown) such that the measurement probe 16 and the further measurement probe 47 simultaneously are connected via the measurement bridge, such that a direct comparative measurement can be carried out, where the measurement probe 16 measures on the component 10 at the same time as the further measurement probe 47 measures on a calibration object 41.

The switching unit 25 and the parts 23, 27, 31, 32, 33 which are included therein are constructed to function in the radioactive environment which can be the case where a measurement on for example fuel rods 10 is carried out. Furthermore, the parts that are included in the switching device 27 are suitably such that they do not significantly contribute to the impedance.

It can be noted that in FIG. 2 it is shown that the first end 22a of the second cable 22 is connected to the switching unit 25 at the casing 35. It is of course also possible that the casing 35 has a lead-through such that the second cable 22 enters through the casing 35 such that the first end 22a of the second cable 22 is directly connected to the switching device (the relay) 27 which is located within the casing 35. In a corresponding manner, also the first cable 21 and the cable 61 may extend in through the casing 35 and be directly connected to the switching device (relay) 27. Also the third cable 23 can of course be directly connected to the switching device (relay) 27. The third cable 23 should of course be connected in such a manner that its characteristics correspond to the characteristics of the second cable 22 (and the characteristics of the cable 61).

According to the invention, the system can be used for measuring for example the thickness of a layer on fuel rods for a nuclear reactor. For example, the thickness of an oxide layer and/or a crud layer can be measured with the help of the system according to the invention. It is also possible to measure for example the hydride content in such fuel rods. The measurement is suitably carried out, as mentioned above, when the fuel rods are located in a water pool.

The invention is not limited to the described examples but can be varied within the scope of the following claims.

The invention claimed is:

1. A system for carrying out eddy current measurements on components for nuclear reactors when these components are located in water, wherein the system is adapted to measure at least one property of these components, such as the thickness of at least one layer located on the component, by generating at least one electromagnetic alternating field which penetrates the component in question and in the same generates eddy currents which retroact on the generated electromagnetic alternating field, wherein the system is arranged to carry out the measurement of the property in question by measuring a response to the generated electromagnetic alternating field and carrying out a calculation of the property in question, wherein the system comprises,
   a control unit located outside of the water and arranged to control the measurement,
   a measurement probe moved to the immediate vicinity of the components in the water, wherein the measurement probe comprises means, preferably at least one coil, with the help of which the electromagnetic alternating field which penetrates the component in question is generated,
   a first cable constituting at least a part of the connection between the control unit and the measurement probe, wherein this cable is at least partially located in the water, and
   a switching unit located in the water and arranged to be connected with said first cable, and to be connected with the measurement probe, wherein the switching unit comprises a switching device which can assume at least a first and a second state, wherein in the first state the first cable is connected with the measurement probe and in the second state the first cable is not connected with the measurement probe.

2. A system according to claim 1, wherein the switching unit comprises at least a first known load and is arranged such that in said second state the first cable is connected with the first known load.

3. A system according to claim 2, wherein the first known load has a known finite impedance value.

4. A system according to claim 3, wherein the known finite impedance value is between 5 Ω and 1000 Ω.

5. A system according to claim 2, wherein the switching unit comprises a second known load, the switching device can assume a third state, and wherein in the third state the first cable is connected with the second known load.

6. A system according to claim 5, wherein the second known load has essentially the impedance value 0 Ω.

7. A system according to claim 5, wherein the switching unit comprises a third known load, wherein the switching device can assume a fourth state, wherein in the fourth state the first cable is connected with the third known load.

8. A system according to claim 7, wherein the third known load has essentially infinite impedance value.

9. A system according to claim 1, comprising a second cable, of a certain length I, wherein one end of the second cable is connected to the switching unit and the other end of the second cable is connected to the measurement probe, wherein in the first state the first cable is connected with the measurement probe via the second cable.

10. A system according to claim 9, wherein the switching unit comprises a third cable, with the same, or at least essentially the same, characteristics as the second cable, wherein the switching device is arranged such that the first cable can be connected to the third cable instead of to the second cable.

11. A system according to claim 10, wherein the third cable has exactly, or at least approximately, the length I.

12. A system according to claim 10, wherein the switching unit is arranged such that in one, two or all of said second, third and fourth states, the first cable is connected with the known load via the third cable.

13. A system according to claim 1, wherein the switching unit has a casing which is constructed not to let in water, such that the parts which are arranged within the casing remain dry when the switching unit is used in water.

14. A system according to claim 13, arranged with means for introducing a gas, preferably air, within the casing when the system is used and the switching unit is located in water, for causing an overpressure within the casing such that water is prevented from penetrating into the inside of the casing.

15. A system according claim 1, comprising a measurement probe holder which is arranged to be able to move the measurement probe to and from the component on which it is to be measured.

16. A system according to claim 15, comprising one or more calibration objects, with known properties, located in the vicinity of the measurement probe holder, wherein the measurement probe holder is arranged to be able to move the measurement probe to said one or more calibration objects for enabling a calibration measurement.

17. A system according to claim 15, comprising remote control means arranged to enable remote control of the movement of the measurement probe holder.

18. A system according to claim 1, comprising a temperature sensor which is adapted to be located next to or in the vicinity of the switching unit or the measurement probe and which communicates with the control unit.

19. A system according to claim 1, comprising a resistance meter, intended to be located outside of the water, and adapted to carry out measurement of direct current resistance, wherein said resistance meter is adapted to be connected with one end of said first cable at the same time as the second end of the first cable is connected to the switching unit.

20. A system according to claim 1, wherein the switching unit and the parts which form part thereof are adapted to function in a radioactive environment of the kind which may be the case during measurement in water on components for nuclear reactors.

21. A system according to claim 1, comprising a further measurement probe adapted to be connected with the switching unit at the same time as the previously mentioned measurement probe is connected to the switching unit.

22. A method comprising:
providing the system according to claim 1,
carrying out the measurements on said components which are fuel rods for a nuclear reactor.

23. The method of claim 22 further comprising:
measuring the thickness of at least one layer on the fuel rods.

24. The method of claim 22 further comprising:
measuring the hydride content in the fuel rods.

25. The method of claim 22 further comprising:
carrying out the measurements when the fuel rods are located in a water pool.

* * * * *